Oct. 29, 1957 R. BAERMAN ET AL Plant Pat. 1,654
GLADIOLUS PLANT
Filed Sept. 12, 1956
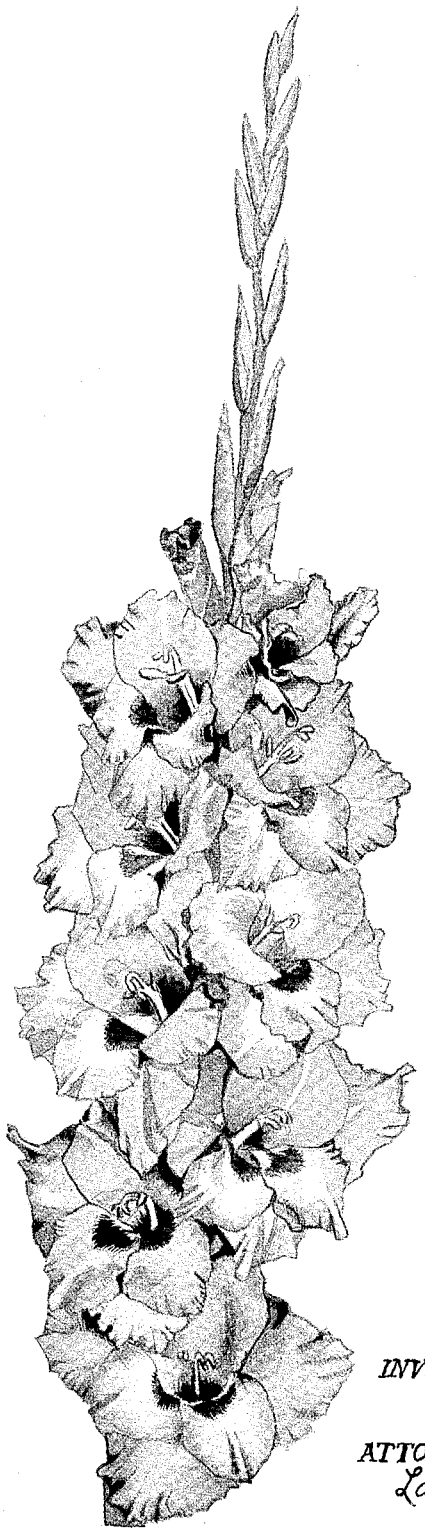
INVENTORS
RALPH BAERMAN
CARL H. FISCHER
ATTORNEY
Lamont Johnston United States Patent Office Plant Pat. 1,654
Patented Oct. 29, 1957

1,654

GLADIOLUS PLANT

Ralph Baerman, Arlington, Va., and Carl Fischer, St. Charles, Minn., assignors to Selected Glads, Inc., Nashville, Tenn., a corporation of Tennessee Application September 12, 1956, Serial No. 609,513

1 Claim. (Cl. 47—60)

Our present invention relates to a new and improved variety of gladiolus plant, and is notable for the size and quantity of bloom, delicate and distinctive coloring, heavy substance of petals, and apparent freedom from disease.

This new variety is the result of a cross between the varieties Beauty's Blush (unpatented) as the seed parent, Better Times (unpatented) as the pollen parent. It was produced by hand pollination done by the first-named inventor in a rented garden near his home when living at Suitland, Maryland, and it exhibits the traits of both parents. It was asexually reproduced in Minnesota by the second-named inventor by natural increase from cormels. Through several generations, its characteristics have proved to be permanently fixed.

The illustration forming a part of this application shows a spike of the bloom of this new variety in approximately its true natural coloring.

In the following detailed description, color plate references are to Ridgway's Color Standards and Nomenclature, edition of 1912. Where there are other references to color, the ordinary dictionary meaning of the term is intended.

*The plant*

Growth: Under ordinary culture, the plant reaches a height of 54 inches. It is an exceptionally rapid propagator and an easy germinator, although the bulblets are small.

Blooming habit: Each spike will hold 8 to 11 florets open at one time outdoors on spikes of 20 to 22 flowers and buds, and florets will not wilt even in 100 degree weather. In addition to the blooms that are open, 6 buds will be showing color. The variety is an early bloomer, flowering from mature No. 1 bulbs in 65 to 70 days, depending on the season.

Disease resistance: Unusually resistant to diseases, such as Fusarium wilt, Sclerotinia dry rot, and Botrytis, to which gladiolus varieties are subject, even when grown alongside another variety which is disease-infested, surpassing any blue variety as to health. This was observed when this variety was grown as a seedling under irrigation in a black loam soil in the vicinity of St. Charles, Minnesota, under the natural conditions provided by the climate of that area. At the end of the season, other varieties and seedlings would succumb to the various diseases, whereas this variety remained hale and hearty.

Stems: Straight, stiff, and wiry; Parrot Green in color (Plate VI); diameter at base averaging nearly an inch.

Foliage: Spinach Green (Plate V); averages 2½ inches wide and 36 inches high, retaining a healthy green color until the bulbs are dug.

Corms: Well-formed, with a moderately high crown and have very heavy husks. Corms from adult plants average 3 inches in diameter.

Spike: Long and slender, bearing 20 to 22 buds and flowers, 3 to 5 of which open the first day, following which 8 to 11 are open at one time until all the buds have opened.

*The flower*

Bud:

*Size.*—Opening buds average 3 inches in length.
*Color.*—Lighter than Pallid Violet (Plate X).
*Opening.*—Eight to 11 florets open at one time with about six additional buds showing color at the same time.

Flower:

*Arrangement.*—Flowers are closely and evenly spaced on the spike and all face in about the same direction.
*Size.*—Average about 3¾ to 4 inches in diameter.
*Form.*—Wide-open, round, regular, and gently recurved; six petals, with one or two throat petals smaller than the others.
*Keeping qualities.*—Flowers keep and ship exceptionally well.

Petals:

*Shape.*—Slightly ruffled.
*Size.*—The larger petals are 2 inches long and 1½ inches wide. The smaller throat petals are 1½ inches long and 1 inch wide.
*Aspect.*—Substance is good.
*Fragrance.*—None.
*Color.*—The predominating color is just a trifle lighter than Pallid Violet (Plate X), the color intensifying to exactly Pallid Violet at the tips of the petals. There is a throat blotch on the central third, usually of the two lower petals, but occasionally of only one, of a Sulphur Yellow color (Plate V), when the floret first opens, but later fading to an Ivory White. On the inner third of the lower petals there is a Hyacinth Violet (Plate XI) blotch. The stamens are Amparo Purple (Plate XI).

Reproductive organs: Stamens—9/16 inch long.

Having thus disclosed our invention, we claim:

The new and distinct variety of gladiolus plant substantially as herein shown and described, characterized particularly by its vigorous growth; its exceptionally rapid propagation; its unusual resistance to disease; its tall, wiry, and slender spikes; its close and even placement of large flowers on the spikes, with all facing in one direction; the large number of florets showing color at one time; and the distinctive delicate Pallid Violet coloring of its flower with a distinguishing Hyacinth Violet blotch on the inner third of the lower petals.

No references cited.